(12) United States Patent
McLaughlin et al.

(10) Patent No.: US 7,220,354 B2
(45) Date of Patent: *May 22, 2007

(54) VORTEX-ENHANCED FILTRATION DEVICES

(75) Inventors: Jennifer K. McLaughlin, Valley Center, CA (US); Don Schoendorfer, Santa Ana, CA (US)

(73) Assignee: KKJ, Inc., Valley Center, CA (US)

( * ) Notice: Subject to any disclaimer, the term of this patent is extended or adjusted under 35 U.S.C. 154(b) by 310 days.

This patent is subject to a terminal disclaimer.

(21) Appl. No.: 10/797,510

(22) Filed: Mar. 10, 2004

(65) Prior Publication Data

US 2004/0238445 A1 Dec. 2, 2004

Related U.S. Application Data

(60) Provisional application No. 60/453,620, filed on Mar. 10, 2003.

(51) Int. Cl.
*B01D 63/16* (2006.01)
*B01D 63/06* (2006.01)
*B01D 61/24* (2006.01)
*B01D 61/00* (2006.01)

(52) U.S. Cl. .......................... 210/321.68; 210/321.63; 210/321.67; 210/321.71; 604/6.09

(58) Field of Classification Search ........... 210/321.63, 210/321.67, 321.68, 321.71
See application file for complete search history.

(56) References Cited

U.S. PATENT DOCUMENTS

| | | | |
|---|---|---|---|
| 4,670,176 A | 6/1987 | Morioka | |
| 4,675,106 A | 6/1987 | Schoendorfer | |
| 4,729,837 A * | 3/1988 | Henricson | 210/784 |
| 4,740,331 A | 4/1988 | Phillips | |
| 4,753,729 A | 6/1988 | Schoendorfer | |
| 4,816,151 A | 3/1989 | Schoendorfer | |
| 4,871,462 A * | 10/1989 | Fischel et al. | 210/651 |
| 4,876,013 A * | 10/1989 | Shmidt et al. | 210/650 |
| 5,000,848 A * | 3/1991 | Hodgins et al. | 210/321.68 |
| 5,034,135 A | 7/1991 | Fischel | |
| 5,194,145 A | 3/1993 | Schoendorfer | |
| 5,738,792 A | 4/1998 | Schoendorfer | |
| 5,900,142 A * | 5/1999 | Maloney et al. | 210/179 |
| 6,099,730 A * | 8/2000 | Ameer et al. | 210/321.67 |
| 6,475,071 B1 | 11/2002 | Joslyn | |

FOREIGN PATENT DOCUMENTS

| | | |
|---|---|---|
| DE | 4015187 | 11/1990 |
| GB | 1480406 | 7/1977 |
| WO | WO 9925463 | 5/1999 |
| WO | WO 03066200 | 8/2003 |
| WO | WO 2004/007048 | 1/2004 |

OTHER PUBLICATIONS

"Experimental Verification of a Model for Rotating Reverse Osmosis"; Sangho Lee and Richard M. Lueptow; Desalination 146 (2002) pp. 353-359.

* cited by examiner

*Primary Examiner*—Krishnan S. Menon
(74) *Attorney, Agent, or Firm*—Knobbe Martens Olson & BearLLP (57) ABSTRACT

Preferred aspects of the present invention relate to a device for filtration comprising at least one rotor configured to create Taylor vortices on at least one side of a filtration membrane, thereby providing substantially enhanced mass or heat transfer across the membrane.

19 Claims, 5 Drawing Sheets

VORTEX-ENHANCED FILTRATION DEVICES

RELATED APPLICATIONS

This application claims priority under 35 U.S.C. §119(e) to U.S. Provisional Application No. 60/453,620, filed on Mar. 10, 2003.

BACKGROUND OF THE INVENTION

1. Field of the Invention

Preferred aspects of the present invention relate to a device that creates Taylor vortices on at least one side of a filter, thereby improving mass transfer and minimizing concentration polarization. Preferred embodiments of the present invention are particularly useful in dialysis of blood from patients with kidney disease. In other embodiments, the present invention can be used in areas of heat and mass transfer.

2. Description of the Related Art

Traditionally, dialysis is the maintenance therapy used to treat kidney disease. There are two common approaches. One is peritoneal dialysis, where the process is done internally to the patient, in the patient's pericardium. Peritoneal dialysis uses the patient's abdominal lining as a blood filter. The abdominal cavity is filled with dialysate, thereby creating a concentration gradient between the bloodstream and the dialysate. Toxins diffuse from the patient's blood stream into the dialysate, which must be exchanged periodically with fresh dialysate.

The second approach is by filtration dialysis. This was initially accomplished using flat sheet dialysis membranes, requiring square meters of the membranes. Devices were large and taxing on patients. In the 1960's, hollow fiber dialysis filtration units became popular. This was an improvement, as a large filter membrane area could be compressed into a small volume, and the volume of blood needed to fill the unit was greatly reduced.

While hollow fiber technology provides a relatively safe and cost effective means for dialysis, problems remain. Manufacturing hollow fiber cartridges is challenging. The patient is still exposed to a large surface area of material foreign to the human system. Many of the chemicals needed in manufacture are toxic to the patient. Cuprophane is the most common membrane material for hollow fiber manufacture, but it has biocompatibility issues, and relatively low permeability performance. There are superior membrane materials available in flat sheet, but these materials are challenging to form into hollow fibers.

One of the most limiting problems in any type of filtration process, including dialysis, is filter clogging, scientifically described as "concentration polarization." As a result of the selective permeability properties of the membrane, the filtered material that cannot pass through the membrane becomes concentrated on the surface of the membrane. This phenomenon is clearly illustrated in the case of a "dead-end" filter, such as a coffee filter. During the course of the filtration process, the filtered material (coffee grounds) building up on the filter creates flow resistance to the filtrate, the fluid (coffee), which can pass through the filter. Consequently, filtrate flux is reduced and filtration performance diminishes.

Various solutions to the problem of concentration polarization have been suggested. These include: increasing the fluid velocity and/or pressure (see e.g., Merin et al., (1980) *J. Food Proc. Pres.* 4(3):183-198); creating turbulence in the feed channels (Blatt et al., *Membrane Science and Technology*, Plenum Press, New York, 1970, pp. 47-97); pulsing the feed flow over the filter (Kennedy et al., (1974) *Chem. Eng. Sci.* 29:1927-1931); designing flow paths to create tangential flow and/or Dean vortices (Chung et al., (1993) *J. Memb. Sci.* 81:151-162); and using rotating filtration to create Taylor vortices (see e.g., Lee and Lueptow (2001) *J. Memb. Sci.* 192:129-143 and U.S. Pat. Nos. 5,194,145, 4,675,106, 4,753,729, 4,816,151, 5,034,135, 4,740,331, 4,670,176, and 5,738,792, all of which are incorporated herein in their entirety by reference thereto). In U.S. Pat. No. 5,034,135, Fischel discloses creating Taylor vorticity to facilitate blood fractionation. Fischel also describes variations in the width of the gap between a rotary spinner and a cylindrical housing, but does not teach variation in this width about a circumferential cross-section.

Taylor vortices may be induced in the gap between coaxially arranged cylindrical members by rotating the inner member relative to the outer member. Taylor-Couette filtration devices generate strong vorticity as a result of centrifugal flow instability ("Taylor instability"), which serves to mix the filtered material concentrated along the filter back into the fluid to be processed. Typically, a cylindrical filter is rotated within a stationary outer housing. It has been observed that membrane fouling due to concentration polarization is very slow compared to dead-end or tangential filtration. Indeed, filtration performance may be improved by approximately one hundred fold.

The use of Taylor vortices in rotating filtration devices has been applied to separation of plasma from whole blood (See e.g., U.S. Pat. No. 5,034,135). For this application, the separator had to be inexpensive and disposable for one-time patient use. Further, these separators only had to operate for relatively short periods of time (e.g., about 45 minutes). Moreover, the separator was sized to accept the flow rate of blood that could reliably be collected from a donor (e.g., about 100 ml/minute). This technology provided a significant improvement to the blood processing industry. The advantages and improved filtration performance seen with rotating filtration systems (Taylor vortices) have not been explored in other areas of commercial fluid separation—including kidney dialysis.

The use of Taylor vortices does not alleviate all problems with filtration however. Another common problem with the use of such rotating filtration devices is concentration polarization on the inner side of the filter membrane. While centrifugal flow instability circulates the fluid between inner and outer members, the rotating inner member does not prevent concentration polarization near the walls of its interior. As a result, filter performance could be further improved by solving this problem of interior concentration polarization.

SUMMARY OF THE INVENTION

In a preferred embodiment, the present invention relates to a device for hemodialysis. The device comprises a cylindrical housing having a housing wall; a first cylindrical rotor having a first wall comprising a dialysis membrane, wherein the first cylindrical rotor is disposed coaxially within the housing and adapted to rotate therein, such that a first coaxial gap exists between the dialysis membrane and the housing wall. There is also included a second cylindrical rotor having a second wall, wherein the second cylindrical rotor is disposed coaxially within the first cylindrical rotor and adapted to rotate therein, such that a second coaxial gap exists between the first and second walls. The device also includes a first inlet port in the housing wall for conducing blood into the first coaxial gap and a first outlet port in the housing wall for conducting dialyzed blood out of the first coaxial gap. A second inlet port is included in the housing for conducting dialysis fluid into the second coaxial gap and a second outlet port is included for conducing dialysate out of the second coaxial gap. The device also comprises first and second rotational drive means for rotating the first and second cylindrical rotors respectively within the cylindrical housing. Consequently, when the first and second rotors are spun, Taylor vortices may be created in the first and second coaxial gaps, thereby enhancing mass transfer across the dialysis membrane and preventing concentration polarization on both sides of the membrane.

In another preferred embodiment, a device is provided for hemodialysis comprising an outer housing having a housing wall, and a first rotor having a first wall comprising a dialysis membrane defining a first interior. The first rotor is disposed within the outer housing and is adapted to rotate therein, such that a first gap exists between the dialysis membrane and the housing wall. The device further comprises a first rotational drive means for rotating the first rotor within the outer housing at a speed sufficient to create Taylor vorticity in the first gap.

In another preferred embodiment, a system is provided for hemodialysis. The system comprises an extraction tube for drawing blood from a patient, and a return tube for returning blood to the patient. The system further comprises a hemodialysis device for extracting waste by-products from blood. The hemodialysis device includes an outer housing having a housing wall and a first rotor having a first wall comprising a dialysis membrane. The first rotor also defines a first interior, and is disposed within said outer housing and is adapted to rotate therein, such that a first gap exists between the dialysis membrane and the housing wall. The hemodialysis device further includes a first inlet port in the housing wall for conducing the blood into the first gap, and a first outlet port in the housing wall for conducting dialyzed blood out of the first gap. The hemodialysis device further includes a second inlet port in the outer housing for conducting dialysis fluid into the first interior and a second outlet port for conducing dialysate out of the first interior. The hemodialysis device further includes a first rotational drive means for rotating the first rotor within said outer housing at a speed sufficient to create Taylor vorticity in the first gap. The system further comprises a separator for extracting plasma water, and a junction at which the plasma water is integrated with the blood.

In another preferred embodiment, the present invention relates to a device to facilitate mass transfer. The device comprises a housing having a housing wall; a first rotor having a first wall comprising a filtration membrane, wherein the first rotor is disposed within the housing and adapted to rotate therein, such that a first gap exists between the filtration membrane and the housing wall. There is also included a second rotor having a second wall, wherein the second rotor is disposed within the first rotor and adapted to rotate therein, such that a second gap exists between the first and second walls. The device also includes a first inlet port in the housing wall for conducing a first fluid into the first gap and a first outlet port in the housing wall for conducting filtered first fluid out of the first gap. The device also comprises first and second rotational drive means for rotating the first and second rotors respectively within the housing. Consequently, when the first and second rotors are spun, Taylor vortices may be created in the first and second gaps, thereby enhancing mass transfer across the filtration membrane and preventing concentration polarization on both sides of the membrane.

In another preferred embodiment, the present invention relates to a device to facilitate heat transfer. The device comprises a housing having a housing wall; a first rotor having a first wall comprising a filtration membrane, wherein the first rotor is disposed within the housing and adapted to rotate therein, such that a first gap exists between the filtration membrane and the housing wall. There is also included a second rotor having a second wall, wherein the second rotor is disposed within the first rotor and adapted to rotate therein, such that a second gap exists between the first and second walls. The device also includes a first inlet port in the housing wall for conducing a first fluid into the first gap and a first outlet port in the housing wall for conducting filtered first fluid out of the first gap. The device also comprises first and second rotational drive means for rotating the first and second rotors respectively within the housing. Consequently, when the first and second rotors are spun, Taylor vortices may be created in the first and second gaps, thereby enhancing mass transfer across the filtration membrane and preventing concentration polarization on both sides of the membrane.

In another preferred embodiment, the present invention relates to a device to facilitate mass transfer from a first fluid. The device comprises a housing having a housing wall, and a rotor having a wall comprising a filtration membrane and defining an interior, wherein said rotor is disposed within said housing and is adapted to rotate therein. The device further comprises a gap between the filtration membrane and the housing wall, wherein the gap has a cross-section with a width varying about a circumference., and a rotational drive means for rotating the rotor within said housing at a speed sufficient to create Taylor vorticity in the gap.

In one embodiment of a method incorporating the present invention, hemodialysis is performed on a patient by providing a hemodialysis device configured to create Taylor vorticity. Blood is introduced from the patient into the hemodialysis device, and a first rotor within the hemodialysis device is rotated to create Taylor vorticity within the blood. Dialysis fluid is introduced into the hemodialysis device, and dialyzed blood is collected from the hemodialysis device for return to the patient.

In another embodiment of a method of performing hemodialysis on a patient, a hemodialysis device is first provided. The device comprises a housing having a housing wall; a first cylindrical rotor having a first wall comprising a dialysis membrane, wherein the first cylindrical rotor is disposed coaxially within the housing and adapted to rotate therein, such that a first coaxial gap exists between the dialysis membrane and the housing wall. There is also included a second cylindrical rotor having a second wall, wherein the second cylindrical rotor is disposed coaxially within the first cylindrical rotor and adapted to rotate therein, such that a second coaxial gap exists between the first and second walls. The device also includes a first inlet port in the housing wall for conducing blood into the first coaxial gap and a first outlet port in the housing wall for conducting dialyzed blood out of the first coaxial gap. A second inlet port is included in the housing for conducting dialysis fluid into the second coaxial gap and a second outlet port is included for conducing dialysate out of the second coaxial gap. The device also comprises first and second rotational drive means for rotating the first and second cylindrical rotors respectively within the housing. Blood is introduced from the patient into the first coaxial gap through the first inlet port. Taylor vorticity is created within the blood by rotating the first cylindrical rotor using the first rotational drive means. Dialysis fluid is introduced into the second coaxial gap through the second inlet port, and Taylor vorticity is created within the dialysis fluid by rotating the second cylindrical rotor using the second rotational drive means. Dialyzed blood is collected from the hemodialysis device through the first outlet port, and dialysis fluid is collected from the hemodialysis device through the second outlet port.

In one embodiment of a method of performing mass transfer from a first fluid, a filtration device is first provided. The filtration device has a housing with a housing wall, and a first cylindrical rotor with a first wall comprising a filtration membrane. The first cylindrical rotor is also disposed coaxially within said housing and adapted to rotate therein, such that a first coaxial gap exists between the filtration membrane and the housing wall. The filtration device also has a second cylindrical rotor with a second wall, wherein said second cylindrical rotor is disposed coaxially within said first cylindrical rotor and adapted to rotate therein, such that a second coaxial gap exists between the first and second walls. The filtration device further has a first inlet port in the housing wall and a first outlet port in the housing wall. The filtration device also has first and second rotational drive means for rotating the first and second cylindrical rotors within said housing. The first fluid is introduced into the first coaxial gap through the first inlet port. Taylor vorticity is created within the first fluid by rotating the first cylindrical rotor using the first rotational drive means. Taylor vorticity is also created by rotating the second cylindrical rotor using the second rotational drive means. The filtered first fluid is collected from the filtration device through the first outlet port.

In one embodiment of a method of performing heat transfer from a first fluid, a filtration device is first provided. The filtration device has a housing with a housing wall, and a first cylindrical rotor with a first wall comprising a membrane. The first cylindrical rotor is also disposed coaxially within said housing and adapted to rotate therein, such that a first coaxial gap exists between the membrane and the housing wall. The filtration device also has a second cylindrical rotor with a second wall, wherein said second cylindrical rotor is disposed coaxially within said first cylindrical rotor and adapted to rotate therein, such that a second coaxial gap exists between the first and second walls. The filtration device further has a first inlet port in the housing wall and a first outlet port in the housing wall. The filtration device also has first and second rotational drive means for rotating the first and second cylindrical rotors within said housing. The first fluid is introduced into the first coaxial gap through the first inlet port. Taylor vorticity is created within the first fluid by rotating the first cylindrical rotor using the first rotational drive means. Taylor vorticity is also created by rotating the second cylindrical rotor using the second rotational drive means. The heat-exchanged first fluid is collected from the filtration device through the first outlet port.

In another embodiment of a method of increasing mass transfer across a semi-permeable barrier, vorticity is created on both sides of the barrier.

DETAILED DESCRIPTION OF THE PREFERRED EMBODIMENT

It is well known that Taylor vortices, otherwise referred to herein as Taylor vorticity, can increase the mass transfer through a filter by one or two orders of magnitude. This is useful where it is desirable to remove a component of a fluid by size separation from a feed fluid. For example, Taylor vorticity is useful in removing plasma from blood. Here the separation mechanism is accomplished by the pore size of the filter.

In other separation processes the components of the feed fluid are removed by following a concentration gradient. An example of this is in dialysis and, in particular, blood dialysis. Here, urea and other low molecular weight waste by-products are removed from blood by placing blood on one side of a membrane and a fluid with low concentrations of urea and other waste by-products on the other side of the membrane. The urea and other waste by-products follow the concentration gradient and move through the membrane from the blood to the dialysis fluid. Alternatively, a combination of pore size and concentration gradient may be used in dialysis. Plasma water moves more freely across a membrane as a result of its small molecular size, and the waste by-products in the blood diffuse across the membrane as a result of their size and the resulting concentration gradient.

The performance of such blood dialysis devices may be improved by using a system that generates Taylor vorticity to diminish concentration polarization and increase mass transfer of low molecular weight waste by-products through the filtration membrane. In one embodiment of the invention, a blood dialysis device that generates such Taylor vorticity may be provided.

As described above, concentration polarization can be a problem on the dialysate side of the membrane as well as the blood side. In preferred embodiments of the present invention, the problems of concentration polarization on both sides of a filtration membrane are solved by creating Taylor vortices on both sides of the membrane. Creating Taylor vorticity on both sides of a filtration membrane comprising a first rotor may be accomplished in accordance with a preferred embodiment of the present invention by providing a second rotating rotor inside the first rotor. This can be used to improve transfer both from a first fluid into the membrane and from the membrane into a gap between the first and second rotors.

Figure 1:
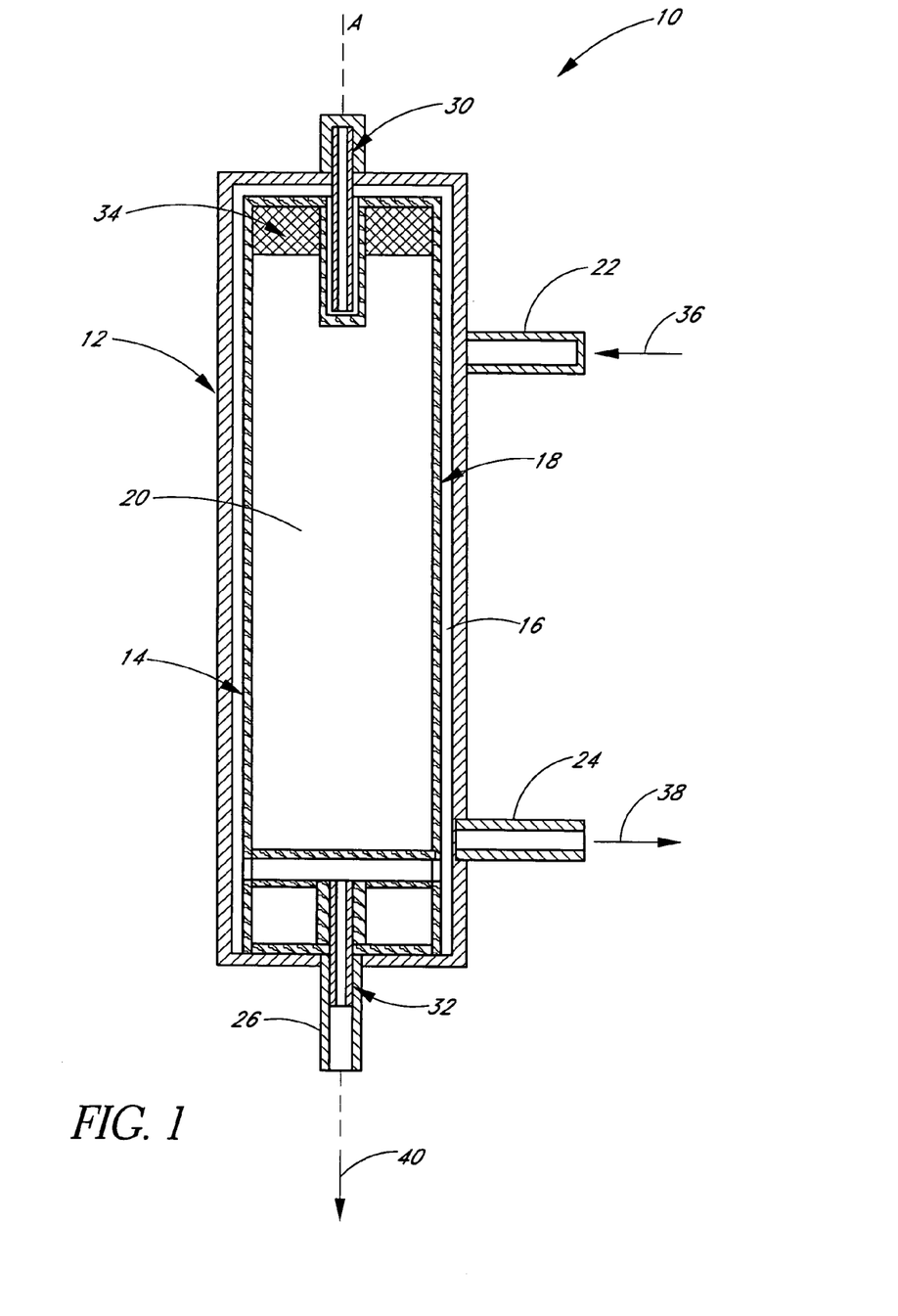
FIG. 1 shows a cross sectional view of one embodiment of a vortex-enhanced dialysis device of the present invention.

FIG. 1 shows a cross section of one possible embodiment of this invention, in which a single rotor device creates Taylor vorticity. In the illustrated embodiment, the filtration device 10 is used to perform hemodialysis, filtering undesirable waste by-products from blood. In other embodiments, the device 10 may be used, more generally, to transfer mass from one fluid to another. In still other embodiments, the device 10 may be used to transfer heat from one fluid to another. As would be well known to those of skill in the art, the invention should not be limited to medical applications.

In one embodiment, the filtration device 10 comprises a cylindrical case 12 housing a cylindrical rotor 14. A gap 16 exists between the case 12 and the rotor 14, and, in a preferred embodiment, the rotor 14 is disposed coaxially within the cylindrical case 12. In other embodiments, different geometries and configurations may be chosen for the case and rotor, to accommodate other fluids and other means of generating Taylor vorticity.

In the illustrated embodiment, the cylindrical, circumferential walls of the rotor 14 are at least partially composed of a filtration membrane 18, and partially define a rotor interior 20. The rotor interior 20 is further defined by the top and bottom walls of the rotor 14, which may or may not comprise filtration membrane. As illustrated in FIG. 1, the filtration membrane 18 is a dialysis membrane, porous for the small to medium-sized molecules that might represent waste by-products present in blood. In a typical application, the dialysis membrane 18 is porous up to a mass of approximately 10,000 Daltons. In other embodiments, varying degrees of filtration and/or heat transfer may be facilitated by the use of different filtration membranes. For example, in a heat transfer application, the filtration membrane may comprise an impermeable structure, which nevertheless is an effective transferor of heat.

In the illustrated embodiment, the cylindrical case 12 has three fluid access ports 22, 24, 26, two 22, 24 leading to the gap 16 between the case 12 and rotor 14, and one 26 leading from the rotor interior 20. In other embodiments, different fluid access configurations may be provided. For example, in one embodiment, only one fluid access port leads to the gap between the case and rotor, and two ports lead to the rotor interior.

In one embodiment, mounted in the axis A of the cylindrical case 12 are two pivot pins 30, 32, one on either end. These pivot pins 30, 32 define the axis of rotation A for the rotor 14, and facilitate the free rotation of this rotor 14. As illustrated, the bottom pivot pin 32 may be hollow, providing fluid transport passage through the case 12 and rotor 14. Of course, in other embodiments, the top pivot pin 30 may also be hollow to accommodate another fluid access port. Other means of facilitating rotation may be provided, including, e.g., ball-bearing assemblies and other means well known to those of skill in the art.

In one embodiment of the invention, the rotor 14 can rotate freely within the cylindrical case 12. In order to control this rotation, a spinner magnet 34 may be mounted internally to the rotor 14, and an external rotating magnetic field (not shown) may be configured to interact with this spinner magnet 34. By modulating the external magnetic field, the magnet 34 and, in turn, the rotor 14 can be made to spin in different directions and at varying speeds. In a preferred embodiment of the invention, the rotor 14 can be spun at a speed sufficient to create Taylor vorticity within a fluid in the gap 16 between the rotor 14 and case 12. By creating Taylor vorticity in this gap 16, filtration performance can be dramatically improved. Other means of spinning the rotor 14 in order to create Taylor vorticity may be used in keeping with this invention, as is known to those of skill in the art. For example, in one embodiment, a motor may be attached to at least one of the pivot pins, e.g. the top pivot pin 30, attached to the rotor 14.

In one embodiment, the rotating magnetic fields that control the rotor 14 can be produced by a series of magnetic coils that surround the filtration device 10 at its top. These electrical coil assemblies can be formed in half arch ("C" sections) that can be closed around the device 10, although other configurations are possible.

The illustrated size of the device 10 is considered adequate for hemodialysis, although in other applications, larger or smaller filtration devices may be utilized to suit the particular fluids being processed.

In a hemodialysis application, the gap 16 between the rotor 14 and inside wall of the case 12 is selected to provide adequate Taylor vorticity in the blood. This gap 16 depends on the diameter and the RPM of the rotor 14, which parameters can be modified by one of skill in the art. With a centrifugal speed in the range of about 1000-5000 RPM and a rotor diameter of about 0.1 to 10 inches, the width adequate to generate Taylor vortices may be in the range of about 0.003 to about 0.3 inches. More preferably, a gap 16 having a width of about 0.03 inches should provide adequate vorticity for a rotor 14 of about 1 inch in diameter spun at about 2,400 RPM.

Figure 2:
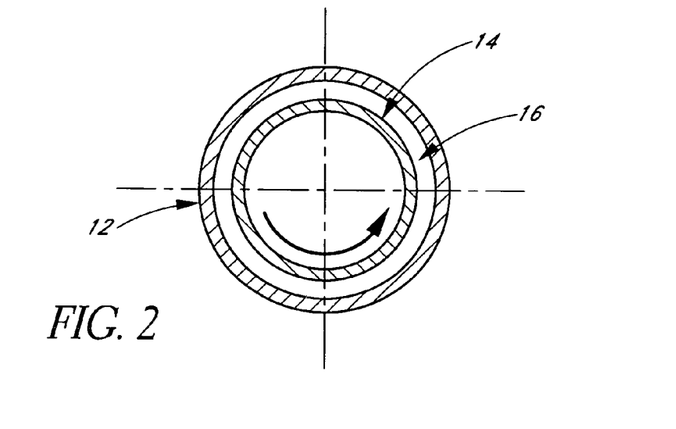
FIG. 2 shows an overhead cross sectional view of one embodiment of the device of FIG. 1.
Figure 3:
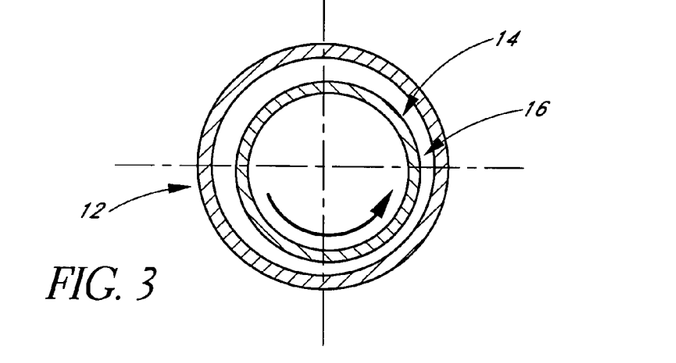
FIG. 3 shows an overhead cross sectional view of a second embodiment of a vortex-enhanced dialysis device.
Figure 4:
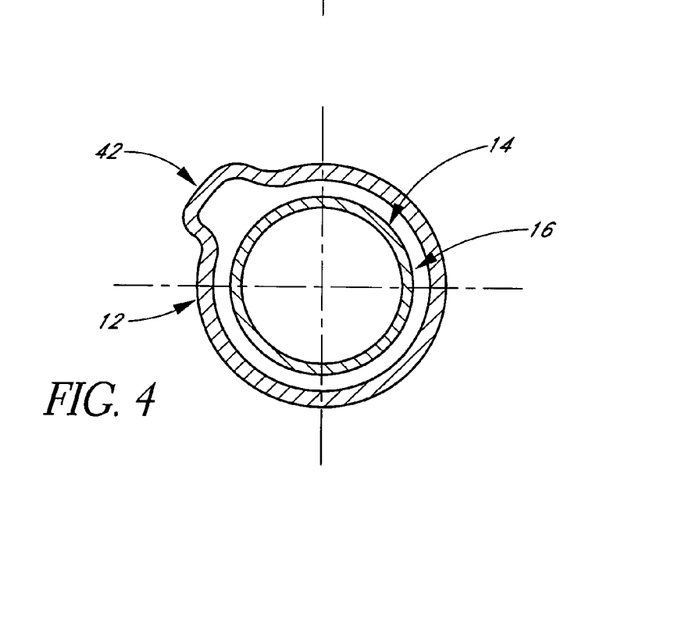
FIG. 4 shows an overhead cross sectional view of a third embodiment of a vortex-enhanced dialysis device.

FIGS. 2-4 illustrate some further structural features of different embodiments of the hemodialysis device described above. In particular, different geometries and configurations of the housing and rotor are shown, which may be implemented to attain various advantages. In FIG. 2, the embodiment described above is shown. As can be more clearly seen in this Figure, the rotor 14 is cylindrical and disposed coaxially within the cylindrical case 12. Thus, the gap 16 is of constant width about the circumference of the device 10. In this relatively simple embodiment, calibrating the appropriate speed of the rotor 14 is more easily accomplished, and the Taylor vortices are fairly constant in strength about the entire filtration membrane 18.

In FIG. 3, another configuration of the case 12 and rotor 14 is shown. In this embodiment, the case 12 and rotor 14 have individual cross-sections similar to those in FIG. 2, but are no longer aligned coaxially. As shown in FIG. 3, the gap 16 therefore varies in width about the circumference of the case 12. Since the Taylor number, reflecting the strength of resulting vortices, is directly proportional to the width of the gap, the sections of rotor 14 farther from the wall of the case 12 experience greater Taylor vorticity than those sections nearer to the wall. As the rotor 14 passes these wider gap locations, residual concentration polarization and any clogging of the filter membrane 18 will be "blown" off by the stronger vortices, opening up blinded zones in the membrane 18. As a result, once per revolution, the longitudinally extending sections of the membrane 18 will be "cleaned" by passing the widened portions of the gap 16, and the efficiency of the device 10 may be improved. In addition, where the width of the gap 16 decreases, the shear forces in the gap increase, and this varying shear force may also tend to increase mass transport across the membrane 18. Thus, once per revolution, we can increase shear and decrease vorticity at any point on the membrane 18 on rotor 14.

In FIG. 4, another configuration of the case 12 and rotor 14 is shown that will similarly create a non-constant width gap. In this configuration, the case 12 and rotor 14 are configured similarly to those in FIG. 2, but the case 12 further has a bulge 42 incorporated into its wall. The gap 16 therefore varies in width about the circumference of the case 12, widening at the site of the bulge 42, producing the advantages discussed above with reference to FIG. 3. The abrupt shift between wide and narrow widths in this embodiment may introduce further vortex characteristics that may facilitate dialysis. In other embodiments, the case 12 and rotor 14 may have other cross-sectional geometries, resulting in a variable width gap 16.

Returning to FIG. 1, one method of implementing the hemodialysis device 10 may be discussed with reference to the Figure. Arrows 36, 38 and 40 show the input and output of the flows into and out of the device 10. In the illustrated embodiment, blood from a patient flows through the gap 16 between the rotor 14 and the case 12, while plasma water and waste by-products are filtered into the rotor interior 20. Due to the concentration gradient between the blood and the plasma water that initially crosses the membrane 18, certain waste by-products will preferentially flow through the dialysis membrane 18 into the plasma water, thereby dialyzing the blood. The rotor 14 spins at a speed sufficient to create Taylor vortices in the blood and prevents concentration polarization in the blood near the dialysis membrane 18. In this way, one embodiment of the present invention enables use of a smaller, more biocompatible hemodialysis device 10.

In further detail, a blood inlet port 22 is located at the top of the cylindrical case 12 and a blood outlet port 24 is located at the bottom. This allows blood to flow from top to bottom simply using gravitational energy, and pressure from the blood influx. The device 10 is preferably designed such that in the time it takes a certain quantity of blood to travel from the top of the hemodialysis device 10 to the bottom, the desired amount of waste by-product has been extracted. A plasma water and waste by-product outlet port 26 is located at the bottom of the rotor 14. In a preferred embodiment, this solution flows out of the device 10 for further filtering as described in further detail below.

In another embodiment, a dialysis fluid may be used to facilitate hemodialysis. Another fluid access port may be added to the top of the device 10 to allow dialysis fluid to enter the device. As is described in detail with reference to FIG. 6, waste by-products diffuse into the dialysis fluid and are carried away from the device by the dialysate flow. Other modifications may also be made in keeping with the present invention.

Figure 5:
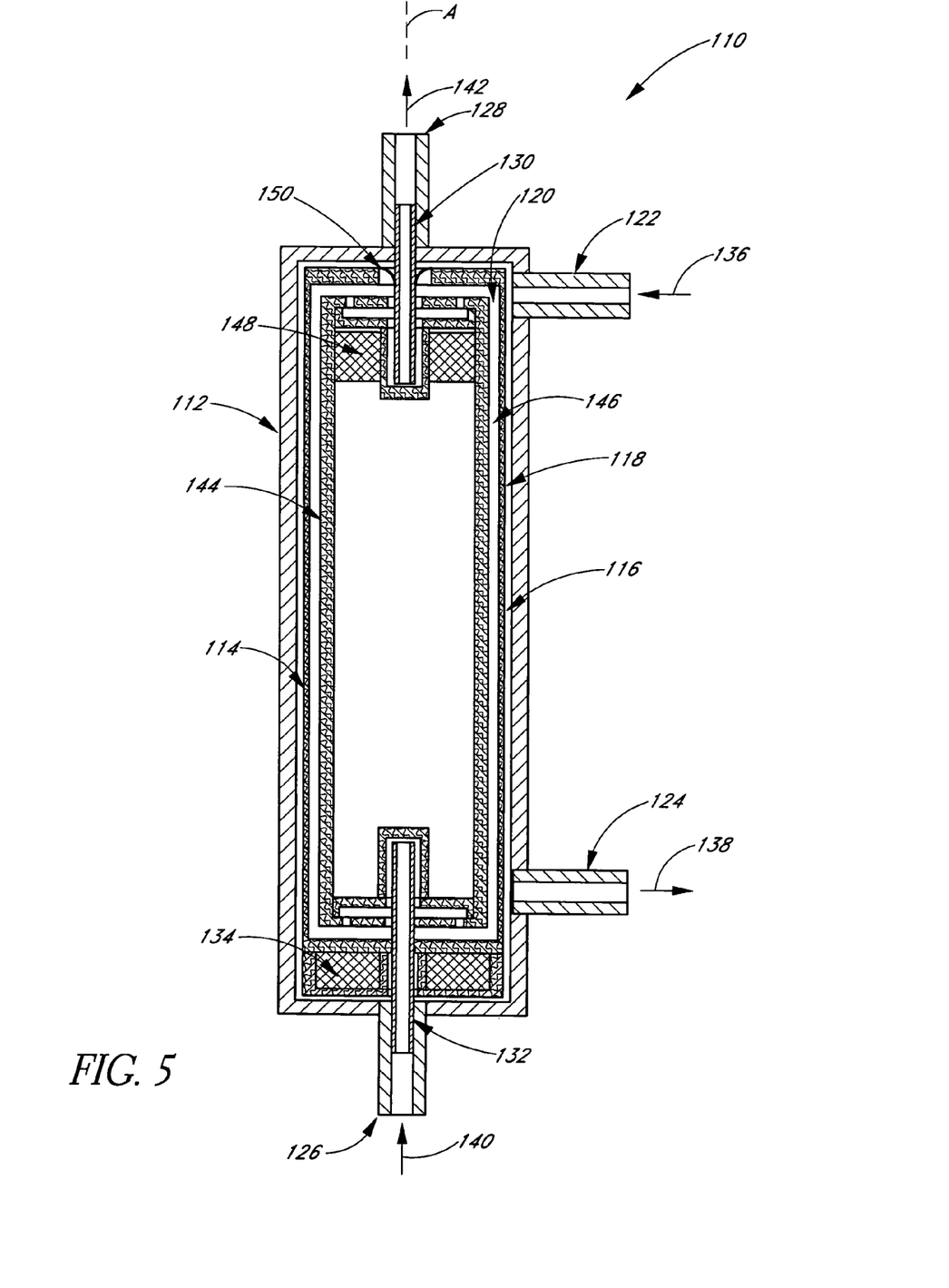
FIG. 5 shows a cross sectional view of one embodiment of a dual rotor vortex-enhanced device of the present invention.

FIG. 5 shows a cross section of another possible embodiment of the present invention, in which a dual rotor device creates Taylor vorticity. In the illustrated embodiment, the filtration device 110 is used to perform hemodialysis, filtering undesirable waste by-products from blood and into a dialysis fluid. In other embodiments, the device 110 may be used, more generally, to transfer mass from one fluid to another. In still other embodiments, the device 110 may be used to transfer heat from one fluid to another. As would be well known to those of skill in the art, the invention should not be limited to medical applications.

In one embodiment, the filtration device 110 comprises a cylindrical case 112 housing a cylindrical outer rotor 114. A first gap 116 exists between the case 112 and the outer rotor 114 through which blood flows, and, in a preferred embodiment, the outer rotor 114 is disposed coaxially within the cylindrical case 112. In other embodiments, different geometries and configurations may be chosen for the case and rotor, as discussed above with reference to FIGS. 2-4.

In the illustrated embodiment, the cylindrical, circumferential walls of the outer rotor 114 are at least partially composed of a filtration membrane 118, and partially define an outer rotor interior 120. The outer rotor interior 120 is further defined by the top and bottom walls of the outer rotor 114, which may or may not comprise filtration membrane. As illustrated in FIG. 5, the filtration membrane 118 is a dialysis membrane. In other embodiments, varying degrees of filtration and/or heat transfer may be facilitated by the use of different filtration membranes. For example, in a heat transfer application, the filtration membrane may comprise an impermeable structure, which nevertheless is an effective transferor of heat.

In one embodiment, mounted in the axis A of the cylindrical case 112 are two pivot pins 130, 132, one on either end. These pivot pins 130, 132 define the axis of rotation A for the outer rotor 114, and facilitate the free rotation of this rotor 114. As illustrated, the pivot pins 130, 132 may also be hollow, providing fluid transport passages through the case 112 and outer rotor 114. In other embodiments, other means of facilitating rotation may be provided, including, e.g., ball-bearing assemblies and other means well known to those of skill in the art.

In one embodiment of the invention, the outer rotor 114 can rotate freely within the cylindrical case 112. In order to control this rotation, a spinner magnet 134 may be mounted internally to the outer rotor 114, and an external rotating magnetic field (not shown) may be configured to interact with this spinner magnet 134. By modulating the external magnetic field, the magnet 134 and, in turn, the outer rotor 114 can be made to spin in different directions and at varying speeds. In a preferred embodiment of the invention, the outer rotor 114 can be spun at a speed sufficient to create Taylor vorticity within a fluid in the first gap 116 between the outer rotor 114 and case 112. By creating Taylor vorticity in this first gap 116, filtration performance can be dramatically improved. Other means of spinning the outer rotor 114 in order to create Taylor vorticity may be used in keeping with this invention, as is known to those of skill in the art. For example, in one embodiment, a motor may be attached to at least one of the pivot pins, e.g. upper pivot pin 130, attached to the outer rotor 114.

Inside the outer rotor 114, an inner rotor 144, also supported by the upper and lower pivot pins 130, 132, may be mounted coaxially, with a second gap 146 created between the two rotors 114, 144. Although the inner rotor 144 may partially comprise another filtration membrane, in a preferred embodiment, the inner rotor is relatively impermeable, simply defining the second gap between the two rotors 114, 144. As described in further detail above with respect to the outer rotor and case, the inner rotor 144 may also have differing cross-sectional geometries, and may be mis-aligned to accommodate other fluids and other means of generating Taylor vorticity. In these alternative embodiments, the inner rotor 144 may be supported by structures other than those supporting the outer rotor 114, and may spin about a different axis.

In a preferred embodiment, the inner rotor 144 rotates freely within both the outer rotor 114 and cylindrical case 112. In order to control this rotation, a second spinner magnet 148 may be mounted internally to the inner rotor 144, and a second external rotating magnetic field (not shown) may be configured to interact with this second spinner magnet 148. In the illustrated embodiment, the second spinner magnet 148 for the inner rotor 144 is located at the top of the device 110, and the spinner magnet 134 for the outer rotor 114 is located at the bottom of the device 110. Thus, two separate and independent magnetic fields can control the rotation of the two rotors 114, 144. As described in further detail above, the second spinner magnet 148 mounted to the inner rotor 144 may be controlled similarly to the one mounted to the outer rotor 114. In a preferred embodiment, the inner rotor 144 can be spun at a speed sufficient to create Taylor vorticity within a fluid in the second gap 146 between the inner and outer rotors. In a further preferred embodiment, the inner rotor 144 is spun in a direction opposite the outer rotor 114 to create even more powerful Taylor vortices. By creating Taylor vorticity in this second gap 146, filtration performance can be further improved, as concentration polarization is prevented on the side of the filtration membrane 118 facing the inner rotor 144. Other means of spinning the inner rotor 144 in order to create Taylor vorticity may be used, as is known to those of skill in the art. For example, in one embodiment, a motor may be attached to at least one of the pivot pins, e.g. lower pivot pin 132, attached to the inner rotor 144.

In one embodiment, the rotating magnetic fields that control the two rotors can be produced by a series of magnetic coils that surround the filtration device 110 at its top and bottom. Since pre-connected tubing (not shown) enters and exits the device 110 on axis A in the illustrated embodiment, these electrical coil assemblies can be formed in half arch ("C" sections) that can be closed around the device 110.

The illustrated size of the device 110 is considered adequate for hemodialysis, although in other applications, larger or smaller filtration devices may be utilized to suit the particular fluids being processed.

In a hemodialysis application, the first gap 116 between the outer rotor 114 and inside wall of the case 112 is selected to provide adequate Taylor vorticity in the blood. This first gap 116 depends on the diameter and the RPM of the outer rotor 114, which parameters can be modified by one of skill in the art. With a centrifugal speed in the range of about 1000-5000 RPM and an outer rotor diameter of about 0.1 to 10 inches, the width adequate to generate Taylor vortices may be in the range of about 0.003 to about 0.3 inches. More preferably, a first gap 116 having a width of about 0.03 inches should provide adequate vorticity for an outer rotor 114 of about 1 inch in diameter spun at about 2,400 RPM.

In the illustrated embodiment, the second gap 146 between the inner and outer rotors is selected to provide adequate Taylor vorticity in the dialysate. This second gap 146 depends on the diameters and the RPM difference between the inner and outer rotors. With a centrifugal speed in the range of about 1000-5000 RPM and an inner rotor diameter of about 0.1 to 10 inches, the width adequate to generate Taylor vortices between the inner rotor 144 and outer rotor 114 may be in the range of about 0.003 to about 0.3 inches. Preferably, a second gap 146 having a width of about 0.03 inches should create adequate vorticity for an inner rotor diameter of about 0.8 inches spun at about 3,600 RPM. This preferred set of parameters would give a rotating speed of the inner rotor 144 relative to the outer rotor 114 of about 1,200 RPM. Alternatively, by spinning the inner rotor 144 in the opposite direction of the outer rotor 114, powerful Taylor vorticity can be created in the dialysate.

For the various potential applications, the dimensions and speeds of the inner and outer rotors and casing may be dramatically different. For example, in certain industrial applications, the filtration device 110 may be designed on a much larger-scale in order to accommodate larger flows and liquids of varying viscosity. Optimizing the ranges of gap and rotor sizes, as well as centrifugal speed and rotor direction can be done by one of skill in the art based on the teaching herein.

In the illustrated embodiment, the cylindrical case has four fluid access ports 122, 124, 126, 128. A first inlet port 122 is located at the top of the cylindrical case 112, and a first outlet port 124 is located at the bottom. In a hemodialysis application, this allows blood to flow from top to bottom through the first gap 116 simply using gravitational energy, and pressure from the blood influx. The device 110 is preferably designed such that in the time it takes a certain quantity of blood to travel from the top of the hemodialysis device 110 to the bottom, the desired amount of waste by-product has been extracted. A second inlet port 126 is located at the bottom of the outer rotor 114, and a second outlet port 128 is located at the top of the outer rotor 114. In the hemodialysis application, the dialysis fluid flows through these ports from the bottom of the device 110 to the top through the second gap 146 between the inner and outer rotors. In this preferred embodiment, the fluid paths are designed to take advantage of counter-current mass transfer, meaning that the paths of blood and dialysate are opposite. Fresh dialysate is exposed through the dialysis membrane 118 with mostly dialyzed blood, where the concentration gradient is the lowest. As is well known to those of skill in the art, however, other numbers and configurations of fluid access ports may be used in keeping with the present invention.

Since the first inlet and outlet ports 122, 124 are on the outer diameter of the case 112, there is no need for high pressure on that flow path. This being the case, in the illustrated embodiment, blood will not be forced to the center of rotation of the outer rotor 114, thus fluid seals are not necessary there to prevent blood from entering the inner rotor 144. Fluid seals can be added if higher fluid pressures are employed in hemodialysis or other applications, or if fluids for filtering enter the inner rotor 144 for any reason.

In a preferred embodiment, the second inlet port 126 for dialysate is configured so that the dialysate passes through the lower pivot pin 132 and is then directed into the second gap 146 between the inner and outer rotors, and not downward into the first gap 116 between the outer rotor 114 and case 112. A fluid seal 150 at the top pivot pin 130 is included in the illustrated embodiment to prevent migration of dialysate into the first gap 116 between the outer rotor 114 and case 112. This seal 150 can be any conventional polymer lip seal. As is well known to those of skill in the art, other seals may be implemented. In an alternative embodiment, another fluid seal is included at the bottom pivot pin 132.

In one method of practicing the present invention, blood is exposed to the dialysis membrane 118 with Taylor vorticity resulting in a minimal concentration polarization layer in the first gap 116 between the outer rotor 114 and case 112, maximizing the ability to remove low molecular weight waste by-products from the patient's blood. In the process of passing through the filtration device 110, dialysate is also exposed to Taylor vorticity, resulting in a minimal concentration polarization layer near the interior of the dialysis membrane 118, maximizing the ability to mix the low molecular weight waste by-products into the dialysate flow.

Figure 6:
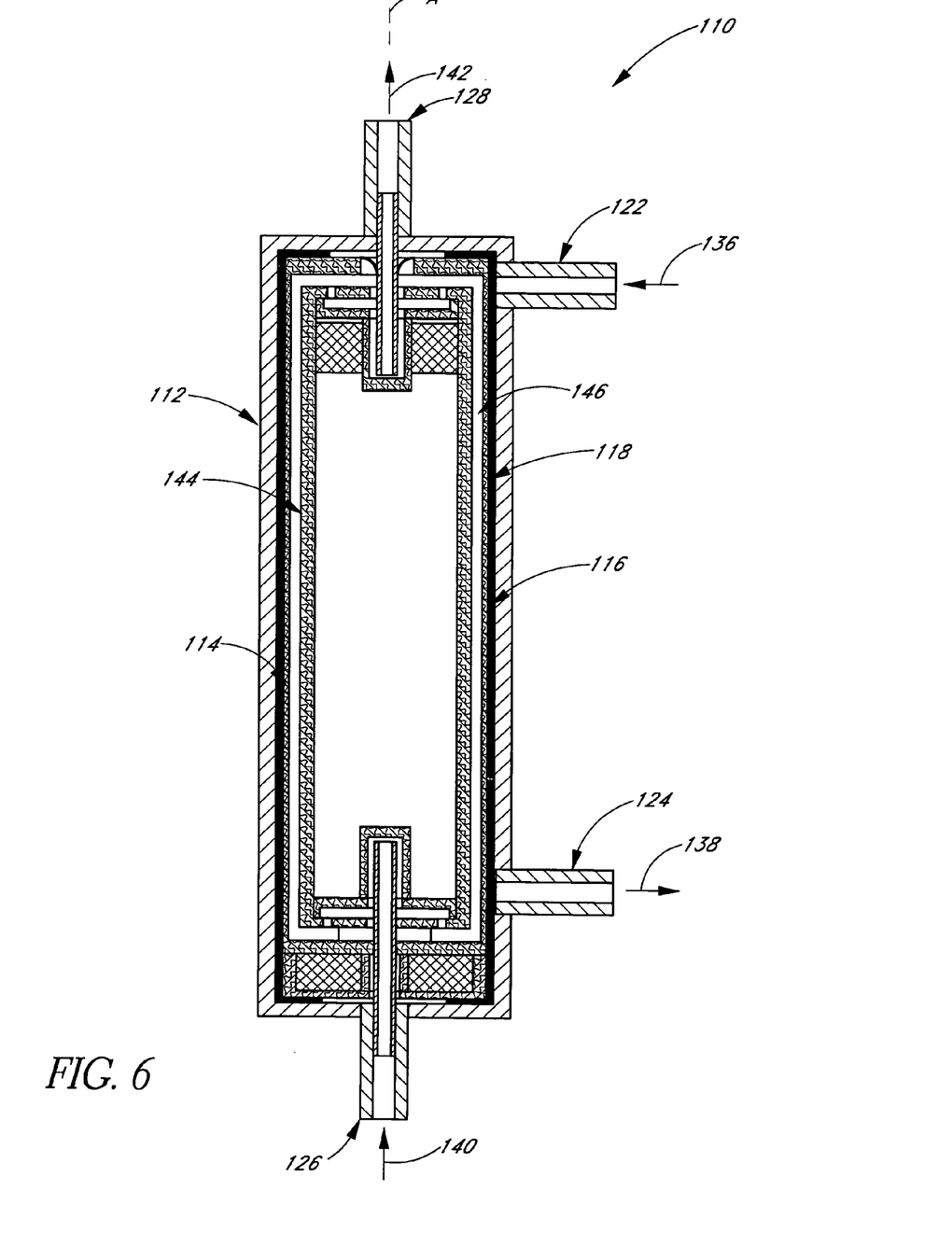
FIG. 6 shows the cross-sectional view of FIG. 5, with the flow-paths of the blood (outer gap) and dialysate (inner gap) highlighted.

In connection with FIG. 6, an exemplary method of performing hemodialysis will be described using the device described in FIG. 5. Within the device 110, the inner and outer rotors are spinning in opposite directions at speeds sufficient to create Taylor vortices in fluids between the outer rotor 114 and case 112, and between the inner rotor 144 and outer rotor 114. Blood is collected from the patient at a particular flow rate 136, and enters the hemodialysis device 110 through the blood inlet port 122, located at the top of the device 110. Dialysis fluid also enters the hemodialysis device 140, but from the bottom, through a second, dialysate inlet port 126. The two fluids are subjected to the forces from the rotors, and Taylor vortices form within them. Thus, concentration polarization is largely alleviated at the dialysis membrane 118 of the outer rotor 114, and a more constant flow of waste by-products travels through the membrane 118 into the dialysate. The dialysate travels through the hemodialysis device 110, within the second gap 146 between the outer and inner rotors, and exits the top through a dialysate outlet port 128, while the dialyzed blood exits through the blood outlet port 124 at the bottom of the device 110 and is returned to the patient.

One problem with both of the above described methods of hemodialysis is that the illustrated dialysis membrane may be porous to water as well as waste by-products. Thus, large volumes of plasma water accompany waste by-products traveling through the dialysis membrane, and the flow of dialyzed blood exiting through the blood outlet port is dramatically reduced from the blood entering the hemodialysis device. In one embodiment, a sterile replacement fluid may be added to the dialyzed blood at a junction prior to return to the patient. However, this embodiment risks patient exposure to contaminated replacement fluid, and increases the costs of hemodialysis by the cost of the replacement fluid.

In another, more preferred embodiment, the patient is used as one source of replacement fluid. This may be accomplished by directing the dialysate, or plasma water emerging from the hemodialysis device through a second separator. The second separator has a membrane of a smaller pore size, selected to allow water and salts to pass through, preferably leaving the waste by-products. The water and salts comprise a biocompatible replacement fluid that can then be added to the dialyzed blood to replace much of the volume lost in the original hemodialysis. In one implementation, the second separator comprises a second filtration device that functions similarly to the hemodialysis device 10 or 110 described above. This second filtration device may differ only in the porosity of the filtration membrane, as its membrane is used to separate water and salts from the rest of the fluid flowing from the device.

In one implementation used with a device configured according to FIG. 5, blood is collected from the patient and flows through a hemodialysis device 110. Dialysate also flows through the hemodialysis device 110 and receives an influx of plasma water as well as waste by-products through the hemodialysis membrane 118. The dialysate flows out of the hemodialysis device 110 into a second filtration device as described above, which acts as a second separator to separate plasma water from the extracted waste by-products. The plasma water extracted in this second filtration device is then combined with the dialyzed blood at a junction and returned to the patient. In some embodiments, not all of the plasma water may be recovered in this system, and so additional replacement fluid must be added to the dialyzed blood prior to return to the patient. However, the volume of artificial replacement fluid is reduced by use of the patient himself as a donor.

It should be further understood that although the second filtration device is described herein as filtering the dialysate flowing from the hemodialysis device 110 and returning the plasma water to the dialyzed blood, it may also filter plasma water out of and back into the system at other locations. For example, in one embodiment, plasma water is filtered out of the dialysate, and that plasma water is then returned to the blood prior to dialysis. Other embodiments using the patient as a donor of replacement fluid may be implemented, as is well known to those of skill in the art.

Figure 7:
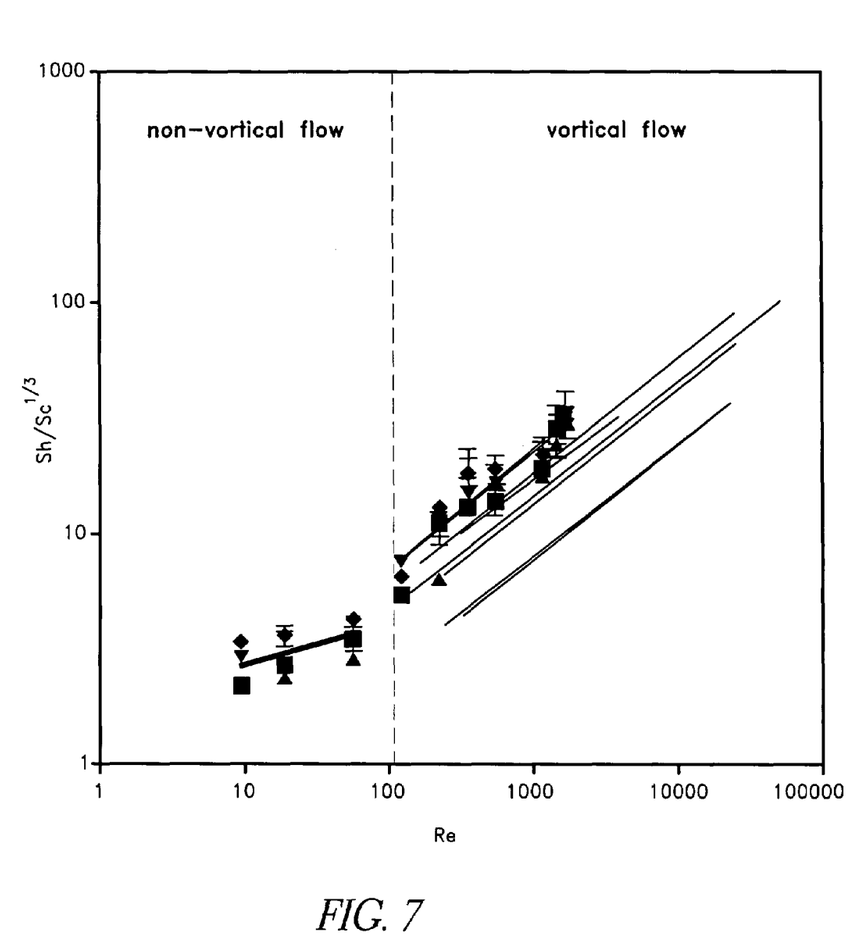
FIG. 7 shows mass transfer correlations in rotating RO. Filled symbols indicate the experimental data. Error bars are smaller than the symbol size except in cases where error bars are shown. Bold lines indicate a least squares fit. (■: NaCl, 6 atm; ▲: NaCl, 8 atm; ▼: NaCl, 10 atm; ♦: $Na_2SO_4$, 10 atm)

With reference to FIG. 7, the benefit of Taylor vorticity can be seen with regard to increasing mass transport across a reverse osmosis (RO) membrane. This figure is derived from the manuscript of Lee and Lueptow, attached hereto and incorporated in its entirety. The results agree with the inventor's observations of the benefit of Taylor vorticity in plasmapheresis. Plasma flux (mass transfer) increased by 100 times over that observed in conventional tangential flow. When applied to the vortex-enhanced devices of the present invention, an increase in the rate of mass transfer of approximately 100-fold should result in approximately a 100-fold reduction in the area of membrane required for effective filtration. Moreover, this design will allow use of hemodialysis membranes of many materials that are not compatible with the conventional hollow fiber geometry (e.g., difficulty in fashioning membrane materials into the hollow tubes).

Those skilled in the art will appreciate that numerous changes and modifications may be made to the preferred embodiments of the invention and that such changes and modifications may be made without departing from the spirit of the invention disclosed herein. It is therefore intended that the appended claims cover all such equivalent variations as may fall within the true spirit and scope of the invention.

What is claimed is:

1. A device for hemodialysis, comprising:
a cylindrical housing having a housing wall;
a first cylindrical rotor having a first wall comprising a dialysis membrane, wherein said first cylindrical rotor is disposed coaxially within said housing and adapted to rotate therein, such that a first coaxial gap exists between the dialysis membrane and the housing wall;
a second cylindrical rotor having a second wall, wherein said second cylindrical rotor is disposed coaxially within said first cylindrical rotor and adapted to rotate therein, such that a second coaxial gap exists between the first and second walls;
a first inlet port in the housing wall for conducting blood into the first coaxial gap and a first outlet port in the housing wall for conducting dialyzed blood out of the first coaxial gap;
a second inlet port in said housing for conducting dialysis fluid into the second coaxial gap and a second outlet port in said housing for conducting dialysate out of the second coaxial gap;
a first rotational drive means for rotating the first cylindrical rotor within said housing; and
a second rotational drive means for rotating the second cylindrical rotor within said housing.

2. The device of claim 1, wherein the first rotational drive means comprises a spinner magnet mounted to the first cylindrical rotor, and an external rotating magnetic field.

3. The device of claim 1, wherein the second rotational drive means comprises a spinner magnet mounted to the second cylindrical rotor, and an external rotating magnetic field.

4. The device of claim 1, wherein the first cylindrical rotor rotates with sufficient speed to create Taylor vorticity in the blood in the first coaxial gap.

5. The device of claim 1, wherein the second cylindrical rotor rotates with sufficient speed to create Taylor vorticity in the dialysate in the second coaxial gap.

6. The device of claim 1, wherein the second wall is impermeable to dialysis fluid.

7. The device of claim 1, wherein the second gap has a cross-section having a variable width.

8. The device of claim 1, wherein the second wall has a generally circular cross-section.

9. A device to facilitate mass transfer from a first fluid, comprising:
- a housing having a housing wall;
- a first rotor having a first wall comprising a filtration membrane, wherein said first rotor is disposed within said housing and adapted to rotate therein, such that a first gap exists between the filtration membrane and the housing wall;
- a second rotor having a second wall, wherein said second rotor is disposed within said first rotor and adapted to rotate therein, such that a second gap exists between the first and second walls;
- a first inlet port in the housing wall for conducting the first fluid into the first gap and a first outlet port in the housing wall for conducting filtered first fluid out of the first gap;
- a first rotational drive means for rotating the first rotor within said housing; and
- a second rotational drive means for rotating the second rotor within said housing.

10. The device of claim 9, further comprising:
- a second inlet port in said housing for conducting a second fluid into the second gap and a second outlet port for conducting the second fluid out of the second gap.

11. The device of claim 9, wherein the first rotor rotates at a speed sufficient to create Taylor vorticity in the first gap.

12. The device of claim 9, wherein the second rotor rotates at a speed sufficient to create Taylor vorticity in the second gap.

13. The device of claim 9, wherein the second wall comprises a second filtration membrane.

14. The device of claim 9, wherein the second wall is impermeable to fluid.

15. The device of claim 9, wherein the first gap has a cross-section having a variable width.

16. The device of claim 9, wherein the second gap has a cross-section having a variable width.

17. The device of claim 9, wherein the first and second walls have generally circular cross-sections.

18. The device of claim 17, wherein the first and second rotors are disposed coaxially within said outer housing.

19. The device of claim 17, wherein the first and second rotors are not disposed coaxially within said outer housing.

* * * * *